United States Patent [19]

Miller et al.

[11] Patent Number: 5,182,039
[45] Date of Patent: Jan. 26, 1993

[54] SYNERGISTIC FLUORINATED ORE FLOTATION AIDS

[75] Inventors: John C. Miller, Hawthorn Woods; William E. Welch, Chicago Heights, both of Ill.

[73] Assignee: Exxon Chemical Patents, Inc., Linden, N.J.

[21] Appl. No.: 677,093

[22] Filed: Mar. 29, 1991

[51] Int. Cl.$^5$ .......................... B03D 1/01; B03D 1/02
[52] U.S. Cl. ...................... 252/61; 562/605; 252/321; 209/166; 209/167
[58] Field of Search .................. 562/605; 252/61, 321, 252/33.6, 34, 51.5 A, 54.6; 209/166, 167

[56] References Cited

U.S. PATENT DOCUMENTS

| | | | |
|---|---|---|---|
| 2,715,107 | 8/1955 | Talley | 252/54.6 |
| 2,941,946 | 6/1960 | Ross | 562/605 |
| 3,269,948 | 8/1966 | Furey | 562/605 |
| 3,284,355 | 11/1966 | Papayannopoulos | 252/54.6 |
| 3,363,758 | 1/1968 | Cronberg et al. | 209/166 |
| 3,404,165 | 10/1968 | Budde et al. | 260/404.5 |
| 3,535,369 | 10/1970 | Sianesi | 562/605 |
| 3,565,926 | 2/1971 | Furey | 562/605 |
| 3,683,010 | 8/1972 | Reck | 562/605 |
| 3,837,489 | 9/1974 | Michalski | 209/167 |
| 4,168,227 | 9/1979 | Polgaire et al. | 209/166 |
| 4,278,533 | 7/1981 | Hefner, Jr. | 209/166 |
| 4,319,987 | 8/1982 | Shaw | 209/166 |
| 4,422,928 | 12/1983 | McGlothin | 209/166 |
| 4,808,301 | 2/1989 | Hansen et al. | 209/167 |

FOREIGN PATENT DOCUMENTS

| | | | |
|---|---|---|---|
| 548123 | 10/1957 | Canada | 562/605 |
| 677816 | 1/1964 | Canada | 562/605 |
| 1009961 | 1/1989 | Japan | 562/605 |
| 2108652 | 4/1990 | Japan | 562/605 |
| 2145550 | 6/1990 | Japan | 562/605 |

Primary Examiner—Peter Hruskoci
Assistant Examiner—Thomas M. Lithgow
Attorney, Agent, or Firm—Jansson & Shupe, Ltd.

[57] ABSTRACT

Flotation aids, for use in ore flotation and beneficiation processes, comprising polyamines in the presence of fluorosubstituted organic compounds, either mixed therewith or at least partially-neutralized thereby, such that the resulting compositions separate silicate impurities and the like while also modifying and/or suppressing the froth generated. The synergistic nature of such compositions, certain embodiments of which are structurally novel, provide a cost-effective route to higher yields and increased production rates.

1 Claim, No Drawings

SYNERGISTIC FLUORINATED ORE FLOTATION AIDS

FIELD OF THE INVENTION

This invention is related generally to ore separation processes and, more particularly, to ore flotation processes which utilize collector agents and the like.

BACKGROUND OF THE INVENTION

In the mining industry, depletion of high-grade ore invariably results in development of methods to utilize ore containing impurities and lower concentrations of the desired mineral. Low-grade, impure ore is concentrated and purified to meet commercial standards, through various processes collectively referred to in the industry as "beneficiation". An overriding concern, of course, is efficiency. Any such method must be cost-effective and competitive with the recovery of naturally high-grade ores.

The mining and purification of iron ore exemplifies this wide-spread phenomenon. Typically, in one common beneficiation process, hematite, magnetite, goethite, or martite-type ore is finely ground to liberate undesirable mineral impurities referred to as "gangue". (Gangue, as found in most iron ore deposits, is a siliceous material such as quartz, clay, etc. and will hereinafter be referred to as silicates, the presence of which adversely affect steel quality and the amount of slag by-product generated in its manufacture.)

The ore or a concentrate thereof is then mixed with water to form a pulp, which is transferred to a large flotation cell equipped with an agitator. Air is introduced into and passed through the pulp. A frothing agent, usually a low molecular weight alcohol, may be used. The froth formed is skimmed-off or allowed to overflow. Undesired silicates float away with the froth, leaving a purer ore concentrate for further processing.

In carrying out the flotation step, a collector agent capable of silicate chelation is added to the pulp. Silicates wetted by the collector agent are hydrophobic and have a surface active affinity for the froth formed. Separation is achieved as the chelated silicates float with the froth to the top of the flotation cell.

The search for an efficient, effective collector agent meeting the requirements stated above has been an ongoing concern in the art. A host of such agents have been developed over the years. While many have been used with some success, most have been limited by poor water dispersability and selectivity, high cost, and general ineffectiveness.

One approach, which has been used with some success, involves the use of various cationic collector agents, including ether amines having the general structural formula

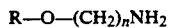

R—O—(CH$_2$)$_n$NH$_2$ where the R—O— portion is derived from a mixture of linear and branched C$_8$ and C$_{10}$ alcohols. Other ether amines have been prepared from higher molecular weight linear and branched alcohols. Regardless, as a matter of practicality and formulation, many such ether amines, as well as their amine analogues, are at least partially neutralized (approximately 30%) with acetic acid, solely to improve water dispersability. (See U.S. Pat. Nos. 4,319,987 and 4,422,928).

Other cationic collector agents used in ore flotation processes include fatty amines, fatty beta-amines, various ether diamines (See U.S. Pat. Nos. 3,363,758 and 3,404,165) and, more recently, blends of alkyl amines/mono ether amines (See U.S. Pat. No. 4,168,227). Again, neutralization (acetic acid) frequently is necessary to effect a satisfactory degree of water dispersability.

However, the prior art has associated with it a number of significant problems and deficiencies. Most are related to inadequate silicate separation and result from the collector agents currently used.

A major problem is that collector agents of the prior art tend to have low selectively. They chelate iron ore, in addition to silicates, removing the iron with the froth. Loss of iron in this manner decreases cost-effectiveness and makes the overall beneficiation process less competitive. Furthermore, iron is entrained in the froth generated, overflows of which result in additional loss of iron.

To counter low selectivity, flotation depressants are sometimes used to inhibit iron chelation and prevent removal with silicate impurities. Starch-type and synthetic depressants enhance iron recovery, but their use is cost-prohibitive.

Collector agents of the prior art also act as emulsifiers, in that they stabilize the froth generated. As a result receiving troughs, pumping reservoirs, and other components experience overflow. Because the froth does not collapse within a reasonable amount of time, severe material handling problems arise.

Transfer of the froth between a series of flotation cells or to other components of the beneficiation process becomes problematical as standard pumping mechanisms are designed to move liquid rather than a gaseous froth. Magnetic separators used to further process magnetite-type ore are also adversely affected, as are tailing thickener operations. Inefficiencies of this nature reduce production rates and increase the overall costs of the beneficiation process.

The aforementioned overflow problems adversely effect plant safety and maintenance. In some instances, redesign of the flotation process is necessary also at great expense.

To compensate for the deficiencies of the prior art, defoamers and collector agents are used in the flotation process. Typically, materials such as silicones, fuel oils or kerosene, or fatty alcohols are added to control the amount of froth produced. The real cost of the collector agent is significantly higher when the price of a defoamer is considered. In such cases, the flotation process must be redesigned to incorporate extra pumping and monitoring components to accommodate use of a defoamer. Furthermore, some defoamers, such as those mentioned above, are odiferous and present numerous worker safety problems.

To circumvent some of the aforementioned concerns, less frothing agent may be used in certain circumstances to decrease the amount of froth generated. However, as a means of compensation, more collector agent is usually employed. The problem then reverts to low selectively and loss of iron ore, raising the overall production cost.

In summary, a considerable number of drawbacks and problems exist in the art relating to the use of collector agents in ore flotation processes. There is a need for an improved flotation aid composition._

OBJECTS OF THE INVENTION

It is an object of this invention to provide an improved ore flotation aid composition overcoming some of the problems and shortcomings of the prior art.

Another object of this invention is to provide an improved ore flotation aid composition for the beneficiation of mineral ores, particularly iron ores.

It is an object of this invention to provide an improved ore flotation aid composition which is highly selective and significantly decreases the amount of iron ore removed with unwanted silicates.

It is an object of this invention to provide an ore flotation aid composition which obviates the need for costly flotation depressants, for those processes in which such additives were previously necessary.

It is an object of this invention to provide an ore flotation aid composition which modifies the froth generated in the flotation process, preventing overflows, reducing plant maintenance, and increasing production rates and cost-effectiveness of the overall beneficiation process.

It is an object of this invention to provide an improved ore flotation aid composition which obviates the need for a separate defoamer used in conjunction with a collector agent.

It is an object of this invention to provide an improved ore flotation aid composition which performs a defoamer function without the need to incorporate extra pumping and monitoring components and without the worker safety problems associated with the prior art.

It is an object of this invention to provide an improved ore flotation aid composition such that it is not necessary to decrease the amount of frothing agent used and concomitantly increase the amount of collector agent employed as a means of compensation.

It is an object of this invention to provide an improved method of ore flotation such that silicates and the like are separated and froth is controlled synergistically without the need for separate introduction of additional of collector agent and defoamer.

These and other important objects will be apparent from the descriptions of this invention which follow.

SUMMARY OF THE INVENTION

This invention includes an improved ore flotation aid composition and method for use in ore separation processes, in particular, froth flotation processes. It overcomes certain well-known problems and deficiencies of the prior art, including those outlined above. An important aspect of this invention is the synergistic nature of the composition, which when used with the method of this invention, allow separation of silicate impurities and the like from mineral ore, while modifying and/or suppressing the froth generated by such processes.

In part, this invention is an ore flotation aid composition including (1) a polyamine having the structural formula $$R(NH_2R'')_nNH_{n'}$$

wherein R is a lipophile selected from the group consisting of $R'C(O)-$, (acyl), $R'-$, (alkyl), and

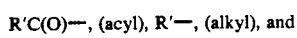

$R'$ is an alkyl chain having 3-26 carbon atoms; $R''$ is an hydrocarbon fragment having 2-6 carbon atoms; a, b, and c are integers from 1-10; n is an integer from 0-4; and n' is an integer from 2-3; and (2) a fluorosubstituted organic compound present in an amount sufficient to modify froth generated in the ore flotation process.

In preferred embodiments of this composition, the organic compound is a fluorinated hydrocarbon, in particular, 1-fluoroheptane. In highly preferred embodiments, the organic compound is a fluorosubstituted carboxylic acid equivalent present in an amount to at least partially neutralize the polyamine and modify the froth generated in the ore flotation process.

In preferred embodiments, the degree of the polyamine neutralization is 0.1-100 mole percent. In highly preferred embodiments, the degree of neutralization is 2-40 mole percent. The most preferred embodiment has a degree of polyamine neutralization of 5-10 mole percent, wherein the acid equivalent is trifluoroacetic acid.

The polyamine lipophile, irrespective of the organic compound component, is preferably alkoxyalkyl. In preferred embodiments, the R' portion of the alkoxyalkyl lipophile has 3-21 carbon atoms. The most preferred embodiment of the composition of this invention is one where the alkoxyalkyl lipophile has an R' portion of 13 carbon atoms, the acid equivalent is trifluoroacetic acid, and the degree of polyamine neutralization is 5-10 mole percent, such that the flotation aid is tridecoxypropylaminopropylamine trifluoroacetate.

Although all compositions of this invention perform as flotation aids, certain embodiments are novel and unobvious without regard to use or application. Such compounds have the structural formula $$[R(NH_2R'')_nNH_{n'}]^{+Y}(X^-)$$

wherein R is a lipophile of the type

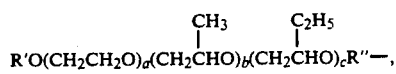

$R'$ is an alkyl chain having 3-26 carbon atoms; $R''$ is an hydrocarbon fragment having 2-6 carbon atoms; a, b, and c are integers from 1-10; n is an integer from 0-4; n' is an integer from 2-3; X is an anion selected from the group consisting of fluorosubstituted carboxylates having 2-4 carbon atoms; and Y is an integer from 1-5 corresponding to the number of anions and degree of neutralization of the alkoxylated ether polyamine.

The method of this invention comprises frothing an ore in an aqueous medium in the presence of 0.01-1.00 pounds (per ton of crude ore) of a flotation aid having the structural formula $$[R(NH_2R'')_nNH_{n'}]^{+Y}(X^-)$$

wherein X is an anion selected from the group consisting of fluorosubstituted carboxylates having 2-4 carbon atoms, and Y is an integer from 1-5 corresponding to the number of anions and the degree of polyamine neutralization. The remaining variables are defined as described above. The flotation aid is present in an amount sufficient to separate silicates and the like from ore and synergistically modify the froth generated in the ore flotation process. In particular, the method of this invention may be utilized when the ore is iron, including hematite, magnetite, geothite, and/or martite-type ores.

With regard to the polyamine component of the flotation aid used with the method of this invention, an alkoxyalkyl lipophile is preferred. Highly preferred lipophiles are those with an R' portion of 3-21 carbon atoms. In preferred embodiments of this method the percent. In highly preferred embodiments, the degree of neutralization is 2-40 mole percent.

As described above, the most preferred embodiment of the method of this invention utilizes a flotation aid wherein the polyamine component has an alkoxyalkyl lipophile with an R' portion of 13 carbon atoms, the anion is trifluoroacetate, and the degree of polyamine neutralization is 5-10 mole percent, such that the flotation aid composition is tridecoxypropylaminopropylamine trifluoroacetate.

An alternate embodiment of the method of this invention utilizes a mixture of (1) a polyamine having the structural formula

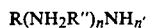

$$R(NH_2R'')_n NH_{n'}$$

wherein each variable is defined as above, and (2) a fluorosubstituted organic compound present in an amount sufficient to modify froth generated in the ore flotation process.

The preferred and highly preferred embodiments of this alternate method may be used with iron ore, in particular, iron ore of the type including hematite, magnetite, geothite, and/or martite. Likewise, the preferred polyamine used in the mixture with the method of this invention is one where the lipophile is alkoxyalkyl, with an R' portion of 3-21 carbon atoms. In highly preferred embodiments, the alkoxyalky lipophile has an R' portion of 13 carbon atoms.

In preferred embodiments of the alternate method of this invention, the fluorosubstituted organic compound is a hydrocarbon, 2-40 percent by weight of the polyamine in the mixture. In highly preferred embodiments, the hydrocarbon is 3-5 percent by weight of the polyamine. The most preferred embodiment of this method uses a mixture of 1-fluoroheptane and tridecoxypropylaminopropylamine.

As previously noted, fluorinated flotation aid compositions and methods for using them in ore beneficiation processes, as revealed through this invention, have certain advantages, most of which relate directly to the presence of a fluorosubstituted organic moiety. Such flotation aids exhibit excellent water dispersibility and selectivity. Compared to collector agents of the prior art a reduced amount of iron ore is entrained and removed with unwanted silicate impurities. In a synergistic fashion, the flotation aids of this invention also promote beneficiation by modifying the froth generated in the ore flotation process. These attributes promote efficiency and higher ore yields in a manner not otherwise obtainable.

Unlike collector agents of the prior art, which actually stabilize froth, the fluorinated flotation aids modify and/or suppress the froth and increase production rates. Less operation time is expended on plant maintenance and related problems associated with froth overflows. Furthermore, in the case of hematite iron ore, it may not be necessary to use either starch-type or synthetic chelation depressants to enhance iron recovery. In this manner, cost-effectiveness is enhanced and, in the case of starch depressants, there is a reduced concern over the growth and proliferation of bacteria or fungi.

Because the flotation aid compositions of this invention modify froth reduced amounts of defoamer and collector agent are needed. In some applications, use of a defoamer may not be necessary at all. Again, cost is decreased and competitiveness enhanced. To the extent some commonly-used defoamers are odiferous, worker safety and related problems are also avoided.

As discussed above, the flotation aids of this invention are distinguished, in part, by the presence of a fluorosubstituted organic moiety, either as a mixture with a polyamine component, or as the anion of a polyamine salt. (As defined herein, "polyamine" is used to describe that component of the ore flotation aid containing the nitrogen functionality; consistant with the structural scheme used, the "polyamine" is a monoamine when n=0.)

A variety of fluorosubstituted carboxylic acid equivalents may be utilized to derive the preferred polyamine salts. The various commercially-available fluorosubstituted acetic, propionic, and butyric acids are useful, as are the analogous acid anhydrides, esters, halides, and other such carboxylic acid equivalents. Trifluoroacetic acid is highly preferred, in that it is readily available, economical, and easily formulated. When used to neutralize a polyamine, it provides a flotation aid composition with excellent water dispersability, chelation selectivity, and froth suppressant properties.

Alternatively, with the same excellent results, the polyamines discussed herein may be used in mixtures with other fluorosubstituted organic compounds, in particular, higher molecular weight fluorohydrocarbons. Typical of such preferred compounds is 1-fluoroheptane. Compounds with lower molecular weights and boiling points tend to be too volatile for ore flotation preocesses. Those with higher molecular weights tend to presnt formulation difficulties. All are readily available through commercial sources or may be prepared by well-known synthetic procedures.

Whether acid-neutralized or part of a mixture, the polyamine component of the composition of this invention may be derived from a variety of fatty precursors. Those having an alkoxyalkyl lipophile with a 3-26 carbon R' portion provide excellent results when used with the flotation processes discussed herein. The preferred alkoxyalkyl lipophiles are those with an R' portion having a range of 3-21 carbon atoms, in any structural configuration. Polyamines in which the R' portion approaches the higher end of this range provide ore flotation aids with less than optimal water dispersibility. The most preferred polyamine components include an alkoxyalkyl lipophile with an R' portion of 13 carbons atoms.

Such polyamines, whether acid-neutralized or present in a mixture with a fluorosubstituted organic compound, provide optimal water dispersablity, selectivity, and defoamer characteristics. The polyamine alcohol precursors may be reacted with alkylene oxides, including ethylene, propylene, and butylene oxides, to provide a variety of polyamines. This, along with a choice of fluorosubstituted organic compounds, allows incorporation of a degree of structural and chemical flexibility into the composition, which may be employed to alter or change any one of the aforementioned properties. An ore flotation aid may be designed especially for use with a given plant operation and ore composition to impart very specific physical and chemical properties to the beneficiation process.

Certain of the preferred alkoxyalkyl mono- (PA) and diamines (DA), as well as their trifluoroacetate derivatives are available from Exxon Chemical Company, Tomah Products Division, of Milton, Wis. As stated above, tridecoxypropylaminopropylamine trifluoroacetate (R' equals 13 carbon atoms) is most preferred (DA-17 trifluoroacetate). Other polyamines discussed herein may be prepared by procedures well-known to those skilled in the art, or are available through various commercial sources.

The amount of the fluorosubstituted organic compound, in combination with a polyamine, effective in providing the desired collector and defoamer functions, is based on amount of polyamine utilized. For example, when acid-neutralized, the degree of polyamine neutralization most preferred is 5-10 mole percent. Less neutralization of a given polyamine, typically results in a lower degree of foam modification, although the collector function may be unchanged. On the other hand, a higher degree of neutralization, toward 40 mole percent, increases foam modification, but the additional cost becomes prohibitive.

Likewise, the preferred mixtures in accordance with this invention contain a fluorosubstituted hydrocarbon in an amount 3-5 percent by weight of the polyamine. In a fashion similar to that described above, less than the preferred amount of fluorosubstituted component generally decreases the foam modification observed. Higher amounts are beneficial, but become cost-prohibitive.

The amount of flotation aid composition used in the froth flotation methods of this invention will vary and be dependent upon such factors as the type of ore mined, the amount of mineral to be collected, the degree of separation required, and most importantly, the chemical composition of the flotation aid, itself. Generally, the amount of flotation aid employed will range from 0.01-1.00 pounds per ton of crude ore. Additional considerations include the type and amount of frothing agent used and the degree to which the froth generated impedes a given ore flotation process. For most applications, use of 0.2-0.3 pounds per ton of crude ore provides excellent results.

Fluorinated compositions used in accordance with this invention would not seem appropriate for use as ore flotation aids. Collector agents of the prior art are acid-neutralized solely to enhance dispersibility in the aqueous systems used. As explained, cost-efficiency and competitiveness are prime considerations in any ore beneficiation. Typical organic and inorganic acids are have been perferred as inexpensive sources of protonation, where no other benefit is sought. These collector agents serve only to chelate unwanted silicate impurities and the like, and it would appear improbable that mixture or neutralization with a a relatively expensive fluorosubstituted organic compound would impart any additional benefit. The use of minor amounts of such compounds in combination with polyamines of the type discussed herein is contrary to the state of the art, and the excellent collector and defoamer characteristics obtained were quite unexpected.

Furthermore, fluorosubstituted organic compounds of the type used in the compositions and methods of this invention are widely thought of a "specialty chemicals". They are of theoretical interest as means for probing the effects of halogen-substitution in various molecular structures. Others, like trifluoroacetic acid and its derivatives, are used largely as analytic reagents or means for functional protection in laboratory-scale synthetic procedures. These factors, coupled with the relative cost factor, make it unobvious to use such fluoro-substituted components in large-scale plant operations.

More particularly, alkoxylated ether polyamine fluorosubstituted carboxylate salts, as described herein, are novel compounds in and of themselves, without regard to use or application. Alkoxylated ether polyamines, alone, are sparingly referenced in the prior art. For the reasons discussed above, their reaction with fluorosubstituted carboxylic acids and their equivalents, would be unobvious, as are the salts thus derived. As with the other compositions of this invention, these compounds are suitable for use as flotation aids.

While not wanting to be bound by theoretical considerations, it may be that the fluorosubstituted organic compounds used in this invention interact with the collector agent (polyamine) and water in some unexpected fashion to impart favorable defoamer characteristics to the ore flotation aid compositions. It is conjectured that introduction of such organic compounds, either in mixture with or to neutralize a polyamine, reduce water surface tension.

In such a way, a two-fold effect on the ore flotation process is achieved. First, lower surface tension enables the silicate surface to be more efficiently wetted, allowing more effective chelation to the polyamine component of the composition. Secondly, lower surface tension at the air/water/polyamine/silicate interface modifies froth formation such that emulsification is retarded and the froth generated is less stable. Larger micelles tend to entrain iron ore during flotation are inhibited, resulting in improved overall iron yields without the process-related problems associated with the prior art.

Preliminary tests indicated the flotation aid compositions of this invention modify/suppress foam, in addition to performing the desired chelation function. Initial data was obtained comparing foam suppression achieved with tridecoxypropylaminopropylamine (DA-17) with various acid-neutralized deratives. In all trials, 1 drop 45% KOH, 1 granule commercial grade $CaCl_2$, and one drop of amine (salt) were added to 50 ml of tap water, which was stirred magnetically for 30 seconds, to ensure suspension of $Ca(OH)_2$. At the conclusion of stirring ($t_0$) each sample prepared in this manner exhibited a generous amount of surface foam. Time and qualitative observations were recorded for each as to the disappearance of foam, as shown in Table 1.

TABLE 1

| Amine | Acid (mole percent neutralization) |
|---|---|
| | Sample 1 |
| DA-17 | None |
| Remarks: | Amount of foam unchanged 30 and 60 seconds after $t_0$. |
| | Approximately 90% of foam remaining 10 min after $t_0$. |
| | Sample 2 |
| DA-17 | Acetic Acid (5%) |
| Remarks: | Amount of foam unchanged 30 and 60 seconds after $t_0$. |
| | Approximately 85% of foam remaining 10 mm after $t_0$. |
| | Sample 3 |
| DA-17 | Trifluoroacetic Acid (5%) |
| Remarks: | Trace amount of foam remaining 30 seconds after $t_0$. |

TABLE 1-continued

| Amine | Acid (mole percent neutralization) |
|---|---|
| | No foam present 60 seconds after $t_0$. |
| | Sample 4 |
| DA-17 | Trifluoroacetic Acid (40%) |
| Remarks: | No foam present 30 seconds after $t_0$. |

PREPARATION OF THE COMPOSITIONS

The preferred tridecoxypropylaminopropylamine trifluoroacetate may be prepared by a variety of methods familiar to those skilled in the art. Using one such synthetic method, tridecyl alcohol (commercially available from Exxon Chemical Company) was cyanoethylated with acrylonitrile to form the ether nitrile, which was catalytically reduced with hydrogen to give the primary ether amine. Repeated cyanoethylation and catalytic hydrogenation provided the desired diamine, a clear yellow liquid with a combining weight of 144.2, corresponding to an average molecular weight of 288.

The diamine (28.2 grams) was mixed with 60 grams of water, before 5 mole percent of trifluoroacetic acid was added with mixing. The exothermic reaction resulted in a clear fluid solution of the diamine trifluoroacetate. (At 5 mole percent neutralization, it is surmised that the predominate neutralized species is the monotrifluoroacetate. As the degree of neutralization is increased toward 40 mole percent the predominate species becomes the ditrifluoroacetate.) Various other flotation aids of the type disclosed herein are prepared in a similar fashion. The compositions of this invention are distinguished by ease of formulation.

Ethoxylated, propoxylated, or butoxylated analogs are prepared in a similar fashion, beginning with the action of potassium hydroxide (approximately 5 grams) on the alcohol precursor. A molar excess of ethylene oxide, propylene oxide, or butylene oxide, respectively, or a combination thereof, is added to the reaction medium over a 2-hour period at 295° F. and 50 psi. The resulting alkoxylated intermediate is stripped under vacuum, cooled, and cyanoethylated, as indicated above, without additional purification.

A number of factors must be considered when preparing compositions for use in ore flotation processes, in accordance with this invention. The concentration of silicate impurities, the type of iron ore, and even the chemical composition of the processed water invariably have an affect on the effectiveness of any flotation aid used. The compositions of this invention incorporate a wide-range of structural and chemical flexibility. A flotation aid may be designed to meet particular use criteria.

EXAMPLES OF THE INVENTION

Listed below are examples of compositions suitable for use as ore flotation aids, in accordance with this invention. All may be used in amounts of 0.01-1.00 lbs per ton of crude ore, including hematite, magnetite, goethite, and martite-type iron ores.

1. PA-14
   (a) 2 mole percent neutralized with trifluoroacetic acid.
   (b) 10 mole percent neutralized with trifluoroacetic acid.
   (c) 50 mole percent neutralized with trifluoroacetic acid.
2. PA-16
   (a) 2 mole percent neutralized with trifluoroacetic acid.
   (b) 10 mole percent neutralized with trifluoroacetic acid.
   (c) 50 mole percent neutralized with trifluoroacetic acid.
3. DA-14
   (a) 5 mole percent neutralized with trifluoroacetic acid.
   (b) 5 mole percent neutralized with heptafluorobutyric acid.
   (c) 40 mole percent neutralized with heptafluorobutyric acid.
4. DA-17
   (a) 5 mole percent neutralized with trifluoroacetic acid.
   (b) alcohol precursor ethoxylated during preparation with 2 moles ethylene oxide, and 40 mole percent neutralized with trifluoroacetic acid.
5. CoCo Diamine
   (a) 50 mole percent neutralized with heptafluorobutyric anhydride.
   (b) alcohol precursor propoxylated during preparation with 5 moles propylene oxide, and 2 mole percent neutralized with trifluoroacetic acid.
6. Tallow Triamine
   (a) 2 mole percent neutralized with pentafluoropropionic acid.
   (b) 5 mole percent neutralized with trifluoroacetic acid.
   (c) 40 mole percent neutralized with trifluoroacetic acid.
7. Tallowamido Triamine
   (a) 25 mole percent neutralized with trifluoroacetic acid.
   (b) alcohol precursor ethoxylated and butoxylated during preparation with 2 moles of ethylene oxide and 10 moles of butylene oxide, respectively, and 5 mole percent neutralized with trifluoroacetic acid.
8. DA-25
   (a) 5 mole percent neutralized with heptafluorobutyric acid.
   (b) alcohol precursor ethoxylated during preparation with 2 moles ethylene oxide, and 10 mole percent neutralized with trifluoroacetic acid.
9. PA-5
   (a) 2 mole percent neutralized with trifluoroacetic acid
   (b) 5 mole percent neutralized with pentafluoropropionic anhydride.
10. DA-10
    (a) 5 mole percent neutralized with pentafluoropropionic acid.
    (b) alcohol precursor propoxylated during preparation with 3 moles propylene oxide, and 10 mole percent neutralized with trifluoroacetic acid.
11. Dododecoxypropyl Pentaamine
    (a) 40 mole percent neutralized with trifluoroacetic acid.
    (b) alcohol precursor ethoxylated and butoxylated during preparation with 2 moles ethylene oxide and 3 moles butylene oxide, respectively, and 10 mole percent neutralized with heptaflurobutyric anhydride.
12. Tallow Tetramine
    (a) 2 mole percent neutralized with trifluoroacetic anhydride.

13. PA-12,14
  (a) 10 mole percent neutralized with trifluoroacetic acid.
  (b) alcohol precursor ethoxylated during preparation with 3 moles of ethylene oxide, and 5 mole percent neutralized with trifluoroacetic acid.
14. Mixture of DA-17 and 1-fluoroheptane
  (a) alcohol precursor of DA-17 ethoxylated during preparation with 2 moles ethylene oxide.
15. Mixture of DA-14 and 1-fluorooctane
16. Mixture of PA-5 and 1-fluoroheptane
  (a) alcohol precursor of PA-5 ethoxylated and propoxylated with 2 moles ethylene oxide and 5 moles propylene oxide, respectively.
18. Cocoamido Triamine and 1-fluoroheptane
  (a) alcohol precursor of the triamine ethoxylated and butoxylated with 2 moles of ethylene oxide and 10 moles of butylene oxide, respectively.
19. Coco Diamine and 1-fluorooctane
  (a) alcohol precursor of the diamine propoxylated during preperation with 5 moles of propylene oxide.

While the principles of this invention have been described in connection with specific embodiments, it should be understood clearly that these descriptions are made only by way of example and are not intended to limit the scope of the invention. For example, the flotation aid compositions described herein may be prepared by post-addition of the fluorosubstituted organic compound (either a fluorinated hydrocarbon or a fluorosubstituted carboxylic acid equivalent) to a flotation cell already containing the polyamine component. Likewise, while the compositions of this invention have described only in connection with iron ore flotation processes, they may be used with other techniques to separate various impurities from for a variety of mineral ores.

We claim:

1. An amine compound having the structural formula

wherein

R is an alkoxyalkyl lipophile of the type

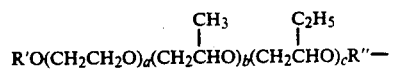

R' is an alkyl radical having 3–26 carbon atoms,
R'' is an alkyl radical having 2–6 carbon atoms,
a, b, and c are integers from 0–10,
n is an integer from 0–4, and
n' is an integer from 2–3,
X is an anion selected from the group consisting of fluorosubstituted carboxylates having 2–4 carbon atoms, and Y is an integer from 1–5 corresponding to the number of anions and degree of polyamine neutralization.

* * * * *

UNITED STATES PATENT AND TRADEMARK OFFICE
CERTIFICATE OF CORRECTION

PATENT NO. : 5,182,039
DATED : January 26, 1993
INVENTOR(S) : John C. Miller and William E. Welch It is certified that error appears in the above-identified patent and that said Letters Patent is hereby corrected as shown below:

In column 1, line 67, delete "solely" and insert --solely--.

In column 3, line 68, delete the formula as it is printed and insert in its place:

--R'C(O)-, (acyl),
R'-, (alkyl), and--

In column 5, line 10, after "the" insert --degree of polyamine neutralization is 0.1-100 mole--.

In column 11, line 10, after Example 15 insert Example 16 as follows: --16. Mixture of DA-17 and 3-fluoroheptane.--.

In column 11, line 11, delete "16" and insert --17--.

Signed and Sealed this

Ninth Day of November, 1993

*Attest:*

BRUCE LEHMAN

*Attesting Officer*   Commissioner of Patents and Trademarks